US009636246B2

(12) United States Patent
Frering (10) Patent No.: US 9,636,246 B2
(45) Date of Patent: May 2, 2017

(54) INFLATABLE AND ADJUSTABLE GASTRIC BAND FOR TREATING OBESITY

(71) Applicant: MEDICAL INNOVATION DEVELOPPEMENT, Dardilly (FR)

(72) Inventor: Vincent Frering, Lyons (FR)

(73) Assignee: MEDICAL INNOVATION DEVELOPPEMENT, Dardilly (FR)

( * ) Notice: Subject to any disclaimer, the term of this patent is extended or adjusted under 35 U.S.C. 154(b) by 338 days.

(21) Appl. No.: 14/350,931

(22) PCT Filed: Oct. 12, 2012

(86) PCT No.: PCT/EP2012/070350
§ 371 (c)(1),
(2) Date: Apr. 10, 2014

(87) PCT Pub. No.: WO2013/053929
PCT Pub. Date: Apr. 18, 2013

(65) Prior Publication Data
US 2014/0257033 A1    Sep. 11, 2014

(30) Foreign Application Priority Data
Oct. 12, 2011    (FR) ..................................... 11 59237

(51) Int. Cl.
*A61F 5/00*     (2006.01)
*B29C 45/16*    (2006.01)

(52) U.S. Cl.
CPC .............. *A61F 5/005* (2013.01); *A61F 5/003* (2013.01); *A61F 5/0056* (2013.01); *A61F 5/0066* (2013.01); *B29C 45/16* (2013.01)

(58) Field of Classification Search
CPC ........ A61F 5/003; A61F 5/0056; A61F 5/005; A61F 5/0066; B29C 45/16
See application file for complete search history.

(56) References Cited

U.S. PATENT DOCUMENTS

| 2007/0016231 A1* | 1/2007 | Jambor ................. A61F 5/0066 606/157 |
| 2008/0294180 A1* | 11/2008 | Frering ................. A61F 5/0066 606/157 |

(Continued)

FOREIGN PATENT DOCUMENTS

| DE | 197 51 733 | 12/1998 |
| FR | 2 887 436 | 12/2006 |

(Continued)

*Primary Examiner* — Christine H Matthews
*Assistant Examiner* — Joshua D Lannu
(74) *Attorney, Agent, or Firm* — Clark & Brody (57) ABSTRACT

An inflatable, adjustable gastric band includes a flexible, hollow, resilient band; and a flexible inflation tube connected to the band and complementary closing means that are capable of mutually engaging so as to lock a ring in a closed position. The ring formed by bringing the distal end and the proximal end of the band together into a slipknot. The hollow band has, in an inoperative position, a preformed curved portion which is extended, by a substantially rectilinear portion, from the proximal end area thereof to the free distal end of the band. The substantially rectilinear portion being suitable for facilitating the insertion of the proximal end of the tube through the loop(s) of the band, and in that the hollow band has, on the outer wall thereof, two loops, said loops being arranged on the substantially rectilinear portion of the hollow band.

18 Claims, 8 Drawing Sheets

(56) References Cited

U.S. PATENT DOCUMENTS

2009/0240269 A1* 9/2009 Denis ................ A61F 5/0066
606/157
2010/0324359 A1 12/2010 Birk

FOREIGN PATENT DOCUMENTS

| FR | 2 903 297 | 1/2008 |
| FR | 2 944 431 | 10/2010 |
| WO | 03/059215 | 7/2003 |

* cited by examiner

FIG. 1

(PRIOR ART)

INFLATABLE AND ADJUSTABLE GASTRIC BAND FOR TREATING OBESITY

TECHNICAL FIELD OF THE DISCLOSURE

The technical field of the invention is that of surgical implants intended to be placed around a segment of the digestive tract in order to narrow the latter, for example between the abdominal part of the esophagus and the stomach. The constriction thus obtained creates, upstream of the stomach, a food retention pouch of much smaller volume than the stomach, such that the signals triggering a feeling of fullness are transmitted earlier to the patient. Such implants are therefore used for treating obesity.

BACKGROUND OF THE DISCLOSURE

Traditionally, these implants can be of the type comprising an elongate hollow body which is inflatable by means of a suitable fluid, for example physiological saline. The surgeon places this hollow body, in an open position, around a segment of the digestive tract situated, for example, between the abdominal part of the esophagus and the stomach.

The surgeon then connects the two ends of the implant to each other in order to lock the resulting ring in a size corresponding to a basal level of constriction of the stomach. The surgeon can then regulate as necessary the level of constriction, hence the weaning of the patient, by inflating/deflating the implanted closed ring from outside the body of the patient with the aid of a syringe and an implantable chamber with septum connected to the ring via a catheter, this regulation being carried out during normal hospitalization.

The technical problems associated with these inflatable and adjustable gastric implants are in particular those mentioned below:
 a. The ease of implantation for the surgeon, which directly influences the comfort and health of the patient.
 b. Further to problem (a), the possibility of performing the implantation by laparoscopy is an important advantage.
 c. Lasting biocompatibility of the implant.
 d. The stresses resulting from the ingestion of food can cause movement of the ring. This can be avoided by means of sutures, although the implanted ring should ideally have a stable position without recourse to this aggressive means.
 e. Visibility to X-rays (radiopacity) is a desired advantage for the implant.
 f. It is also desirable that this type of inflatable gastric implant is not subject to a phenomenon of occlusion, by the inner wall, of the inflation opening which is connected to the catheter and is arranged on the outer wall of the hollow band, particularly during deflation of this hollow band by aspiration of the inflation fluid.
 g. The safety and reliability of closing the hollow band in a ring shape around the stomach of the patient is also a factor in determining the efficacy of the implant. To this end, it is therefore desirable to obtain optimal locking of this closed position.
 h. The demands of serial production according to high quality standards and at the best possible cost are also at the heart of the problems addressed by the present invention.
 i. In order to ensure a centripetal deformation of the closed gastric ring by inflation, it is important that the back or the outer wall is reinforced in relation to the inner wall, of which the outer face is in contact with the digestive tract after implantation.

French patent FR2887436 B1 discloses an inflatable gastric belt comprising an elongate tubular body made of elastically deformable, flexible material, this body defining an inflatable leaktight chamber and having a back and a working face. This belt also comprises connecting means which are arranged in relation to two ends of the tubular body and allow the gastric belt to be closed in the shape of a ring, the working face being arranged on the inside of the ring. This belt finally comprises an inflation catheter which is intended to be connected to inflation means, and which is connected in a leaktight manner to the inflatable chamber via an inflation orifice formed in the back of the elongate tubular body. The inner face of the back of the tubular body has eight protuberances intended to provide support for the inner wall of the chamber near the inflation orifice formed in the back of the tubular body.

The gastric belt according to French patent FR2887436 B1 can be perfected in respect of all or some of the abovementioned technical problems (a) to (i), in particular as regards (a) the ease with which the surgeon places the implant around the stomach, and, more particularly, for introducing the catheter into the loops in order to form the ring around the stomach in a loop formation.

Figure 1:
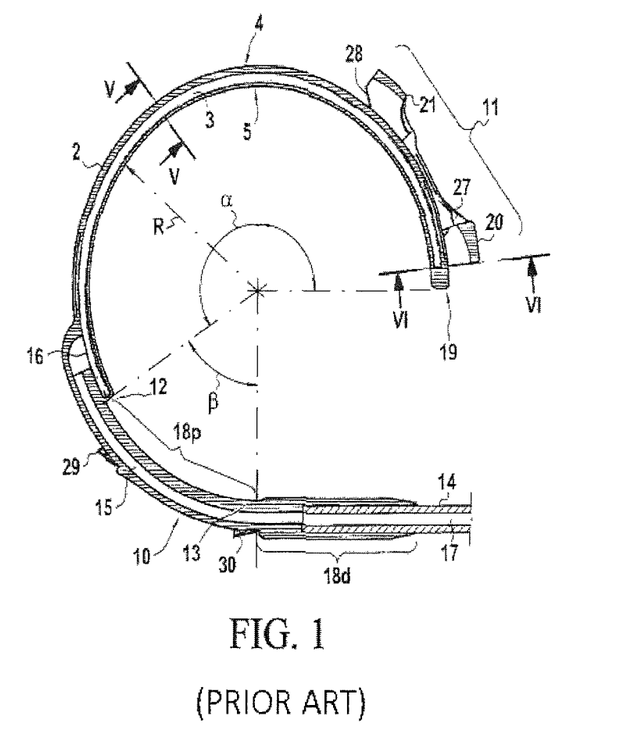
FIG. 1 shows a prior art gastric belt.
Figure 2:
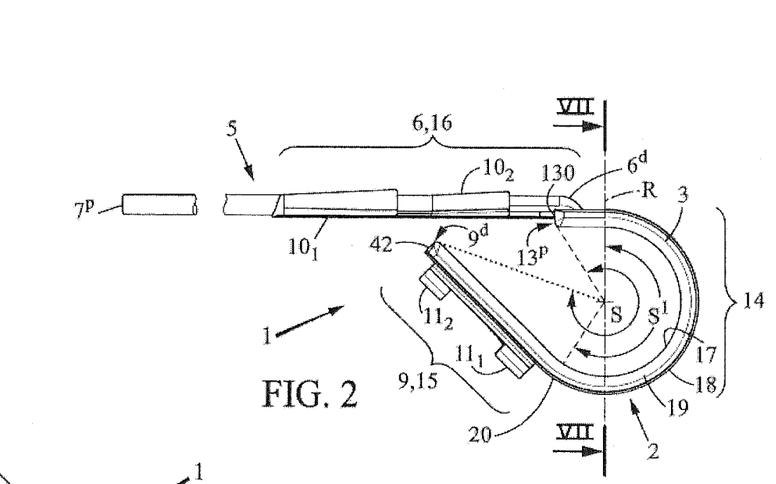
FIG. 2 is a side view of the gastric band according to the invention when not in use, in the deflated state and in the open position (without the hollow flexible band and the tube being engaged in each other to form a loop)

Referring to FIG. 1, French patent FR2903297 discloses a gastric belt 1 comprising a tubular body 2 defining a leaktight and inflatable chamber 3 and having, seen from above, the general shape of a C, as is shown in the attached FIG. 1, which is a cross section in the medial longitudinal plane of the gastric belt according to French patent FR2903297; when not in use and in the deflated state, the tubular body 2 has a generally flat shape and a rectangular cross section. The gastric belt also comprises an inflation catheter 14 via which an inflation orifice 16, formed in the back 4 of the tubular body 2, is connected to inflation means. One of the ends of the catheter 14 is intended to be passed through two arches 20, 21 arranged on the back 4 of the tubular body 2, in the curved free end part thereof, in order to form a ring by looping around the stomach. The end part 18p of the catheter 16 comprises two fir-tree-shaped non-return means 22, which are intended to cooperate with the arches 20, 21 in order to lock the ring in the closed position. The end part 18p of the catheter 16, which comprises these non-return fir trees 22, is bent about an angular sector β of 45 to 75° of the same radius of curvature and in the continuation of the arc of a circle formed by the tubular body on a tubular sector α of between 160 and 230° C. This gastric belt according to French patent FR2903297 B1 can also be perfected in respect of all the abovementioned technical problems a to i, in particular as regards the ease with which the surgeon places it around the stomach, in particular for engaging the proximal free end of the catheter in the loops provided on the distal end part of the hollow body intended to form a ring by looping.

The application WO03/059215 A1 describes a gastroplasty ring preformed in a C shape when not in use, made of an elastomeric material and connected to an inflation catheter. This relatively rigid toric ring is intended to be closed around the stomach of the patient. The ring has an inflatable annular compression chamber which is delimited by a dorsal (external) U-shaped reinforcement on which so-called "lateral" walls (inner part) are overmolded in order to form an assembly which is presented as being "in one piece", but which in reality is not, since it is composed of several overmolded components (discontinuity of the materials). The dorsal reinforcement is made of a material of greater hardness than that of the inner part of the ring. The closure means with a single lock consist of a female means formed by a collar integrally connected to the end of the ring and by a male means formed by an endpiece integrally connected to the other end of the ring. When not in use, this collar and this endpiece are not in the continuation of the pre-formed C-shaped ring.

This ring has the disadvantage of not really being in one piece, of being difficult to produce, and of having only a single closing lock, which increases the risks of accidental opening and the complications associated therewith.

Moreover, this ring has a not inconsiderable thickness and a certain rigidity due to its method of manufacture by preforming. Its placement around the stomach is an awkward and risky operation since it requires the entire ring to be passed under (behind) the stomach, with risks of damage to the spleen and/or the portal vein near the stomach. In addition, the rigid endpiece provided for closing this ring protrudes in the locked position and also has rigid tongues, such that there are real risks of injury to the organs around the stomach of the patient.

In this context, the object of the present invention is to improve the surgical implants of the types described in the patents FR2887436 B1, FR2903297 B1 and WO 03/059215 A1 as regards the abovementioned technical problems.

In particular, the inflatable and adjustable gastric band according to the invention is aimed at ensuring the best possible comfort and safety of the patient, in particular by making the work of the surgeon easier in order to permit rapid and safe placement of the ring around a given segment of the digestive tract. The closed ring implanted in this way must be stable in its position, non-aggressive and effective.

In order to optimize the inflation, hence the adjustment of the level of constriction, the gastric band according to the invention must have a reinforcement of the dorsal outer wall such that the inflation is effected optimally in a centripetal manner.

It is also desirable that deflation does not cause the inflation orifice of the outer wall to be occluded by the inner wall as a result of a reduced-pressure phenomenon during the deflation.

The present invention is also aimed at optimizing industrial manufacture with high demands on quality and economy.

BRIEF DESCRIPTION OF THE INVENTION

These aims, among others, are achieved by the present invention, which relates to an inflatable and adjustable gastric band to be positioned around a segment of the digestive tract in order to narrow the latter, said gastric band comprising:
  a hollow flexible band, which is resilient and comprises an inner wall and an outer wall defining an inflatable leaktight chamber with an inflation opening;
  a flexible inflation tube whose distal end is connected to the inflation opening of the band, and whose proximal end is intended to be connected to inflation means;
  the tube and the band being provided, in the respective distal end areas and thereof, with complementary closure means that are able to mutually engage so as to lock a ring in a closed position, said ring being formed by bringing the distal end and the proximal end of the band together according to the principle of a slip knot, in particular around the segment of the digestive tract to be narrowed; the closure means of the tube being chosen from among notches and the closure means of the band being chosen from among loops, such that the proximal end of the tube is intended to be engaged through the one or more loops of the band as far as a locked closure position once at least one notch and preferably at least two notches are brought beyond at least one loop, preferably at least two loops;
wherein
  the hollow flexible band, when not in use and when the tube and the band are not engaged in each other to form the ring, has a preformed curved part which extends starting from the proximal end area thereof and which is continued via a substantially rectilinear part to the free distal end of the band, said substantially rectilinear part being suitable for facilitating the engagement of the proximal end of the tube through the one or more loops of the band, and
  the hollow band has, on the outer wall thereof, at least one loop, preferably at least two loops, said one or more loops being arranged on the substantially rectilinear part of the hollow band.

DEFINITIONS

The proximal end of the flexible tube is its free end nearest to the outside of the body of the patient in whom the implant is placed, that is to say the free end intended to be connected to the inflation/deflation means.

The distal end of the flexible tube is the end opposite its proximal end, this distal end being connected to the proximal end of the hollow band of the gastric band according to the invention.

The proximal end of this hollow band is therefore the end of the hollow band nearest to the flexible tube.

The distal end of the hollow band is its free end opposite its proximal end.

The term hardness D1, D2 designates the Shore A hardness of the one or more constituent materials of the gastric band, and in particular of the hollow flexible band.

The term flexible band designates a device that is substantially thin when it is not in use, that is to say not inflated.

The expression in one piece designates a product that is made as a single part, preferably obtained with the aid of a sequential multi-injection mold guaranteeing the fusion of the molded materials constituting the product, preferably silicones, and the continuity of said materials. Such a product made in one piece is obtained without overmolding, that is to say with a continuum of molded material.

Preferred Features and Advantages of the Invention

The particular curved and then rectilinear shape of the gastric band according to the invention, and in particular of the hollow band, when not in use and when the tube and the hollow flexible band are not engaged in each other to form the ring, simplifies its placement around the stomach, and the formation of a loop by engaging the proximal free end of the flexible tube in the one or more loops (or vice versa) is promoted by the rectilinear shape of the distal part of the hollow band. The rectilinear part of the distal part of the hollow flexible band is sufficiently long to carry at least one loop, preferably at least two loops, on the outer wall and to help the surgeon close the gastric band by passing the free end of the tube through at least one loop, preferably at least two loops. The gastric band is fitted in place in several steps under laparoscopy and general anesthesia:
  1) the proximal end of the flexible tube is passed round the right-hand lateral region of the stomach, then under the stomach (posterior to the stomach), in order to reemerge in the left-hand lateral region of the stomach (patient positioned facing the surgeon performing the operation), 2) the flexible tube is unwound by pulling the proximal part of the tube outward from the body of the patient, so as to bring the hollow flexible band around the stomach, 3) the rectilinear part of the hollow flexible band is positioned, folded across the anterior face of the stomach, such that the one or more loops on its outer wall face the surgeon performing the operation, 4) the proximal end of the flexible tube is engaged, in a single rectilinear maneuver, through the two loops in order to close the gastric band, 5) the proximal end of the tube is pulled until the one or more notches of the distal part of the tube engage in the one or more loops of the outer wall of the rectilinear part of the hollow flexible band.

Under laparoscopy, the preforming of the hollow flexible band has the advantage of permitting natural positioning of the gastric band around the stomach, without the physician needing to turn the distal part of the hollow flexible band across the anterior face of the stomach. This therefore avoids one maneuver by the surgeon, thereby making implantation easier and also ensuring the safety of the patient, since the operating field is particularly awkward, and minimizing the movements of the surgical tools thus minimizes the risks of the surgery.

Moreover, still under laparoscopy, the fact that the hollow flexible band has a rectilinear part in its distal region affords the advantage of making the gastric band easier to fit in place and, in particular, to close. The engagement of the proximal end of the flexible tube through the one or more loops of the rectilinear part of the outer wall of the hollow band can be done in one maneuver and all at once when these are on the same axis. Indeed, if the distal part of the hollow flexible band were curved, the surgeon performing the operation (under laparoscopy), seeking to close the gastric band, would have to pass the proximal end of the tube through the first loop on one axis, then recover the proximal end of the tube and pass it through the second loop on another axis. As has been mentioned above, the more the surgical maneuvers are minimized, the easier the gastric band is to fit in place, and the greater the safety of the patient. Thus, it is clear that having two loops on the same axis, that of the rectilinear part of the distal part of the hollow flexible band, facilitates the implantation and minimizes the risks of the surgery.

Finally, the fact that, in a preferred embodiment, the rectilinear part in the distal part of the hollow flexible band has, on its outer wall, at least two loops also affords additional safety for the patient. Firstly, the gastric band closed using a single loop could open out, which poses a risk to the patient and necessitates a further surgical intervention. Secondly, the gastric band closed using a single loop twists and risks being the wrong way round on the stomach, the outer wall then being in direct contact with the stomach. The flexible gastric band could then damage the stomach via the loops or notches or could cause erosion or migration in the stomach, which is dangerous.

Advantageously, the length of the rectilinear part of the distal part of the hollow flexible band when not in use, that is to say when not inflated, is between 10 and 40%, more preferably between 17 and 35%, still more preferably between 21 and 33% of the total length of the hollow flexible band.

For example, the length of the rectilinear part is 4.5 cm, and the length of the flexible band is 18.5 cm. The length of the rectilinear part thus represents 24.3% of the length of the hollow flexible band.

The length of the band is measured from the distal end to the proximal end of the hollow flexible band.

Advantageously, the distance between the two loops (measured between the proximal part of the loop closest to the proximal end of the band and the distal part of the loop closest to the distal end of the band) carried by the rectilinear part of the distal part of the hollow flexible band when not in use, that is to say when not inflated, is between 10 and 40%, more preferably between 17 and 35%, still more preferably between 21 and 33% of the total length of the hollow flexible band. For example, the distance between the two loops is between 16 and 34 mm±1 mm, and the length of the flexible band is between 108 and 122 mm±1 mm. The distance between the two loops thus represents between 12 and 32% of the length of the hollow flexible band.

According to a preferred embodiment of the invention, the axis of this substantially rectilinear part, extending as far as the distal free end of the hollow flexible band, intersects the distal end area of the tube.

To further improve the efficacy of this curved shape with a rectilinear prolongation of the hollow flexible band, it is preferable that the distal end area of the tube has a substantially rectilinear part when not in use and when the tube and the hollow band are not engaged in each other to form the ring.

In this latter advantageous alternative embodiment, it is preferable that, when not in use and when the tube and the hollow band are not engaged in each other, the angle A formed by the substantially rectilinear distal part of the hollow band and the substantially rectilinear distant part of the tube is defined as follows in °, according to an increasing order of preference:

A≤60
A≤50
20≤A≤50
40≤A≤90
A=45.

For example, this angle A is measured in the following way: the hollow flexible band is brought without stress into a position in which the hollow flexible band is substantially perpendicular, give a few centimeters, for example between 1 and 5 cm, to a support plane (e.g. the top of a table). This hollow flexible band is then released on the support in such a way that the tube rests on the support in a substantially rectilinear direction in the continuation of the proximal end of the hollow flexible band, so as not to stress the latter to a position other than that which it adopts after being released, as explained above.

In a particularly preferred embodiment, the proximal end area of the hollow band is substantially rectilinear.

According to another distinguishing feature of the invention, one which facilitates the closure of the gastric band, the preformed curved part is at least partially circular, and the angular sector S defined, from the center of this circle, between the proximal end and the distal end of the band is defined as follows in °, according to an increasing order of preference:

S>230; S≥240; S≥250; S≥260; S≥270; S≥280; S≥290; 330≥S≥300; 320≥S≥310.

A distinguishing feature is that the radius of curvature R of this circle is within the following intervals in mm and in an increasing order of preference [10-21]; [13-20]; [14-19]; [15-18]; [17-18].

In a preferred embodiment of the invention, the hollow flexible band of the gastric band has a length to width ratio of between 4.5 and 5.9.

For example, the width of the hollow flexible band of the gastric band is approximately 22 mm±1 mm, and the length of the hollow flexible band of the gastric band is between 108 mm and 122 mm±1 mm, i.e. a length to width ratio of between 4.65 and 5.85.

In order to improve the quality of the adjustment of the constriction of the stomach by inflation of the gastric band, provision is made, according to a distinguishing feature of the invention, that the hollow flexible band is in one piece and is produced from at least two materials M1, M2, the material M1 constituting at least part of the outer wall, and the material M2 constituting at least part of the outer wall. M1, M2 are preferably chosen from silicone elastomers and differ from each other at least in terms of their respective hardness D1, D2, with D1>D2, and more particularly in a preferably increasing order, D1>1.1 (D2); D1>1.2 (D2); 2(D2)>D1>1.3(D2).

In a preferred embodiment, the hollow flexible band as described above, composed of two materials M1 and M2 and having at least two loops on its outer wall in its rectilinear part, is made in one piece.

One of the main features of the invention lies in the choice of the dimensions and materials constituting the gastric band, which offer great flexibility. This flexibility is such that the gastric band can be introduced, with Karl Storz® laparoscopy forceps, through a 12-mm laparoscopy trocar from Covidien®. This is not possible with the gastric bands of the prior art, which are too rigid and can only pass through trocars larger than the 12-mm trocar.

This flexibility is advantageous on several levels:
- it permits the use of a trocar of only 12 mm, which reduces the risks of eventration, herniation or poor healing after an operation by laparoscopy,
- it also makes it possible to reduce the risks of damage to the tissues and organs surrounding the stomach during placement of the gastric band around the latter and also during the time it is placed there.

The term flexible used in the present application corresponds to the flexibility as defined above. Thus, the hollow band according to the invention can be characterized as a flexible band since it can be introduced via said laparoscopy forceps into said 12-mm trocar.

It is important that the gastric band, once implanted, can be seen by the surgeon via a customary medical imaging device, such as X-rays. To do this, it is therefore advantageous that the gastric band according to the invention is partially radiopaque. Preferably, the longitudinal edges of the outer wall are protuberant and, still more preferably, are at least partially radiopaque, especially to X-rays.

Figure 5:
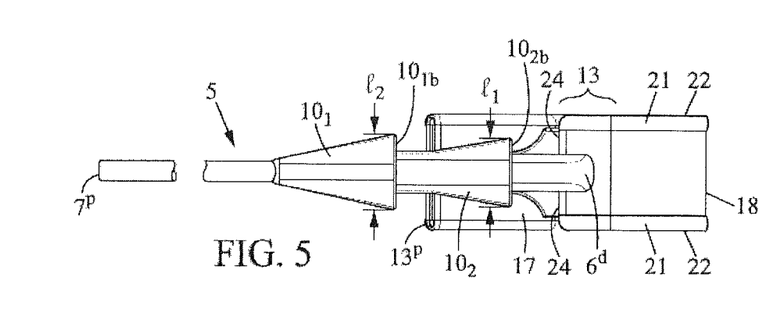
FIG. 5 is a top view of FIG. 2.
Figure 6:
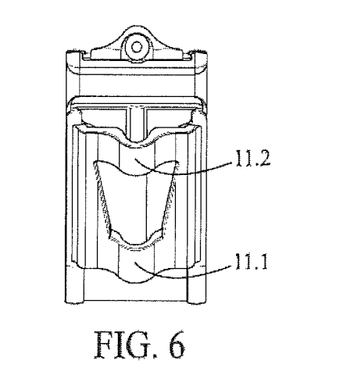
FIG. 6 is a side view of FIG. 2 from the left.

Once the proximal free end of the flexible tube is engaged in the substantially rectilinear free distal end part of the hollow flexible band and is closed in order to form a ring according to the principle of the slip knot, said ring must be able to be locked in the closed position. For this purpose, the distal end area of the tube comprises at least two notches arranged in series $10_1$ & $10_2$ and of dovetailed shape, of which the bases $10_{1b}$ & $10_{2b}$ are of different widths, the width $l_1$ of the notch $10_2$ nearest to the distal end being less than or equal to the width $l_2$ of the other notch $10_1$ (FIG. 5). As has been mentioned above, the distal rectilinear part of the hollow flexible band is able to guide the surgeon when closing the gastric ring and thus facilitates this closure. Since the one or more loops are on the outer wall of the hollow flexible band, the closure of the ring takes place when the notches of the tube have passed beyond their corresponding one or more respective loops. Thus, the tube will cover the distal part (rectilinear when not in use, and curvilinear when the gastric band is in place around the stomach) of the hollow flexible band. This has the additional advantage of limiting the risks of perforation or of damage of the organs around the stomach during the placement and closure of the ring. The inflation tube of the devices of the prior art is most often placed substantially perpendicular to the distal part of the ring or at least not tangential to the latter. For the closure of the gastric band according to the invention, the tube thus runs along the outer wall of the rectilinear part of the hollow flexible band until it locks in a closed position, for example the dovetailed notches being passed through the one or more loops.

In a preferred embodiment of the invention, when the gastric band is closed, either inflated or not, the respective proximal and distal ends of the hollow flexible band come into contact with each other. Thus, when the gastric band is placed around the stomach, the latter is in contact only with the inner wall of the hollow flexible band, without any protuberance. Once formed, the device is thus atraumatic in respect of the stomach and the surrounding organs.

According to another advantageous embodiment of the invention, the inflation opening of the hollow flexible band is formed in the outer wall thereof, near the proximal end area thereof.

In addition, this outer wall advantageously has, on its inner face, recesses, preferably grooves, still more preferably parallel longitudinal grooves and/or parallel transverse grooves, at least some of these recesses being arranged on each side of the inflation opening, said recesses being intended to prevent an occlusion of the inflation opening by the inner wall of the hollow flexible band opposite this opening, especially during deflation.

Preferably, at least one of the longitudinal edges of the hollow flexible band is blunted or rounded.

Preferably, the width of the inner wall of the hollow flexible band according to the invention, whether inflated or not, does not exceed the width of the outer wall of the hollow flexible band, that is to say it does not protrude on either side of the latter.

Preferably, the gastric band is obtained by molding with the aid of a mold, of which the characteristics define said gastric band.

Preferably, the gastric band according to the invention is obtained by sequential multi-injection within one and the same mold.

The invention also relates to the mold itself and to the method for obtaining the gastric band by molding with the aid of said mold, the molded component being obtained, preferably in one piece, by sequential multi-injection within one and the same mold.

In the mold, the shape of the gastric band is characterized by an angle A (in degrees) between the substantially rectilinear distal part of the hollow flexible band and the substantially rectilinear distal part of the tube, so that, according to an increasing order of preference:

A≤60
A≤50
20≤A≤50
40≤A≤90
A=45.

In the mold, the shape of the preformed curved part of the gastric band is at least partially circular, and the angular sector S defined, from the center of this circle, between the proximal end and the distal end of the hollow flexible band is defined as follows, in an increasing order of preference:

S>230,
S≥240,
S≥250,
S≥260,
S≥270,
S≥280,
S≥290,
330≥S≥300,
320≥S≥310.

According to another of these aspects, the invention relates to the use, in a gastric band of the type according to the invention, of recesses, preferably grooves, still more preferably parallel longitudinal grooves, at least some of which are arranged on each side of the inflation opening; these recesses being formed in the inner face of the outer wall that also comprises the inflation opening, in order to prevent an occlusion of the inflation opening by the inner wall of the hollow flexible band opposite this opening, especially during deflation.

The invention also relates to a kit for surgically narrowing a segment of the digestive tract, preferably the stomach, said kit comprising:

as gastric band as defined in the present application;
and an inflation module equipped with a septum and intended to be connected to the proximal end of the flexible tube, in order to permit in situ injection or extraction of an inflation fluid for inflating or deflating the hollow flexible band.

In view of all these aspects, the invention represents a significant advance in the field of gastric implants for treating obesity. The most striking benefits are the assistance provided in surgery, which assistance increases the level of safety, and the convenience of industrial manufacture via the economic and efficient production of a molded one-piece assembly comprising at least two materials, or even three materials, e.g. with the aid of multi-injection molds.

BRIEF DESCRIPTION OF THE DRAWINGS

Other distinguishing features of the gastric band according to the invention will become clear from the following description of a preferred embodiment. This detailed description is made with reference to the attached figures, in which.

DETAILED DESCRIPTION OF A PREFERRED EMBODIMENT

The gastric band according to the invention is designated by the general reference sign 1 on the attached figures.

This inflatable gastric band 1, adjustable around a segment of the digestive tract in order to narrow the latter by constriction, has a hollow flexible band 2 produced from a resilient material, for example a silicone elastomer. This hollow band 2 is elongate and has a substantially rectangular shape in cross section. This hollow flexible band 2 has a substantially rectilinear part 13 having a proximal end 13P, then a curved part 14, which is continued by a substantially rectilinear part 15 having a distal end $9^d$ and carrying closure means 11.

The proximal end part 13P of the hollow flexible band 2 is connected to a flexible inflation tube 5 and more precisely to the rectilinear part 16, with distal end $6^d$, of said flexible tube 5 equipped with closure means 10 matching the closure means 11 of the flexible hollow band 2, which are preferably carried on the outer wall of the distal rectilinear part of the hollow band.

Figure 8:
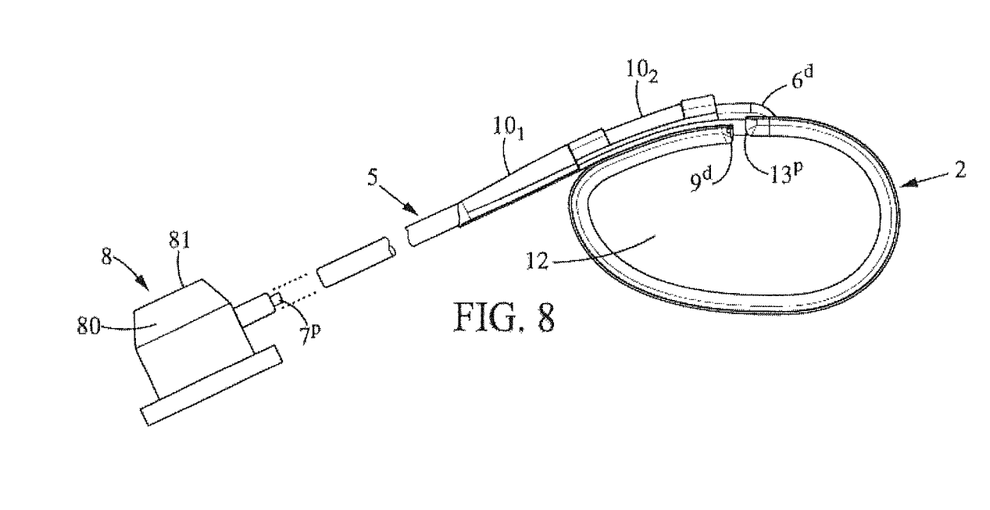
FIG. 8 is a front view of the gastric band according to the invention in the closed position and the deflated state, the proximal end of the flexible tube of this gastric band being connected to an inflation/deflation module equipped with a septum.
Figure 9:
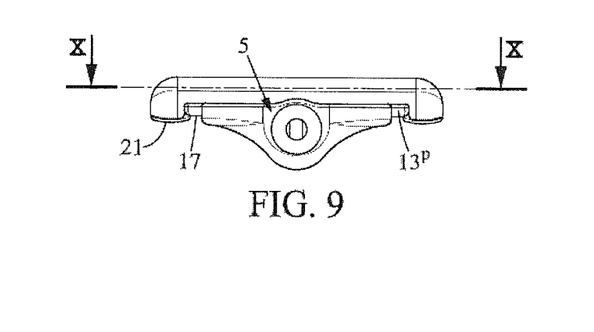
FIG. 9 is a side view of FIG. 2 in which the gastric band is held flat and in which the inner wall has been omitted in order to show the inner face of the outer wall of the gastric band and, in particular, the anti-collapse grooves provided on said inner face.

The flexible inflation tube 5 has a free proximal end $7^P$ intended to be connected to inflation means 8, which themselves comprise an inflation module 80 shown in FIG. 8, are equipped with a septum and permit the injection of inflation liquid or the aspiration of inflation liquid with the aid of a syringe.

The Hollow Flexible Band 2:

The hollow flexible band 2 comprises an inner wall 17 and an outer wall 18 connected to each other by two lateral walls 19 and two end walls, being respectively a proximal end wall 130 and a distal end wall 90, which define a substantially parallelepipedal chamber 30.

This hollow band 2 has the general shape of a hook with a preformed curved part 14, for example substantially circular, characterized by an angular sector S of between 320 and 310° defined, from the center of the circular part, between the proximal end $13^P$ and the distal end $9^d$ of the band 2.

Figure 7:
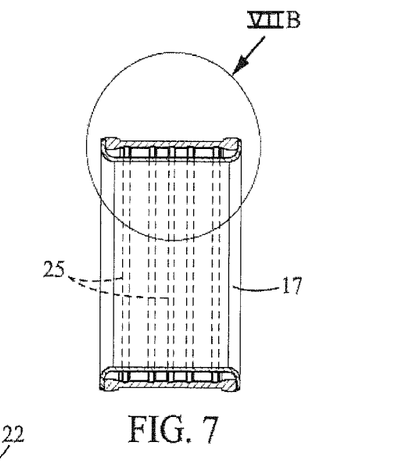
FIG. 7 is a cross-sectional view along the line VII-VII in FIG. 2.
Figure 7B:
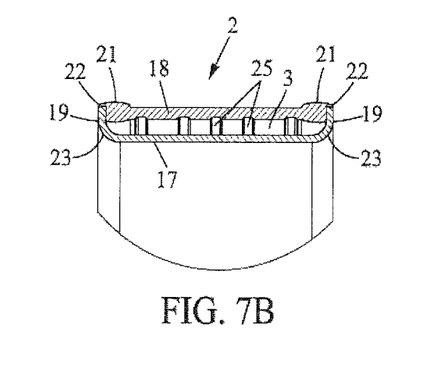
FIG. 7B is an enlarged detail VII of FIG. 7.

As regards the circular preformed curved part itself, its angular sector $S^1$, which extends between the intersection of the axis VII-VII with the hollow band 2 at the end of the area 13 with proximal end $13^P$ and the start 20 of the part 15 with free distal end $9^d$ of this band 2, is between 180 and 270°. Moreover, the axis of the rectilinear part 15, with free distal end $9^d$, of the hollow flexible band 2 intersects the rectilinear part 16, with distal end $6d$, of the flexible tube 5, in such a way as to make it easier for the surgeon to wind the hollow band 2 around the stomach.

Figure 10:
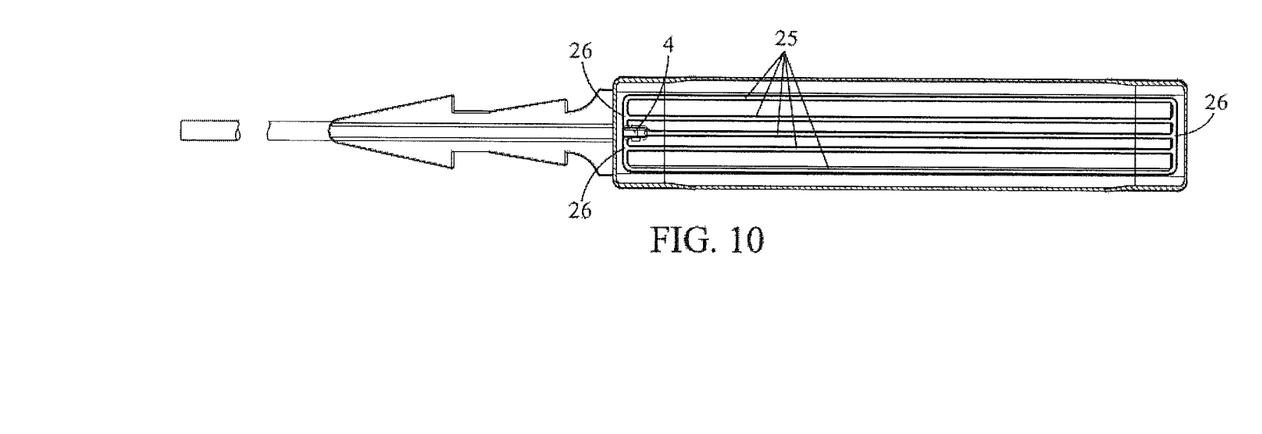
FIG. 10 is a longitudinal sectional view along the line X-X in FIG. 9.

As is shown in particular in FIG. 10, the inner face of the outer wall 18 has parallel longitudinal grooves 25, and two parallel transverse grooves 26 located at the ends of this inner face. Moreover, an inflation opening 4 connecting the flexible tube 5 to the interior of the hollow flexible band 2 is formed in the outer wall 18 close to the proximal end $13^P$. The transverse groove 26 provided at this end is arranged on each side of the opening 4, likewise the nearby terminal parts of the longitudinal grooves 25. These grooves 25, 26 make it possible in particular to prevent occlusion of this opening 4 during deflation as a result of a reduced-pressure phenomenon applying the inner wall 17 against the opening 4 in order to close it.

In this example, the closure means 11 arranged on the outer wall 18 of the hollow flexible band 2 are preferably in the form of loops $11_1$, $11_2$. These loops are preferably at least two in number. It is of course possible to provide other suitable means to ensure proper closure of the gastric ring. Moreover, still according to the example illustrated, and in order to promote this passage of the flexible tube and to reduce as far as possible the forces needed for this surgical maneuver, the loops have, on their inner face, a series of striations which reduce the contact surface of the flexible tube with the corresponding loop, so as to reduce the frictional forces. These striations extend parallel to the longitudinal axis of the hollow flexible band 2 and in the direction of introduction of the flexible tube 5.

The hollow flexible band and the loops that it carries are made in one piece, that is to say they form a single component.

Figure 3:
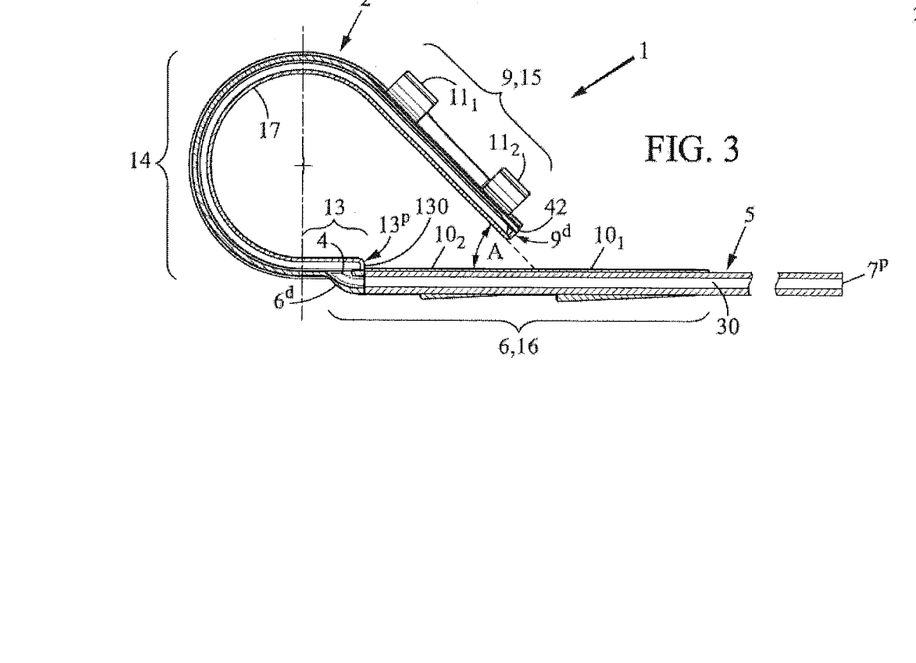
FIG. 3 is a sectional view of FIG. 2 in the median longitudinal plane (line III-III in FIG. 4)
Figure 4:
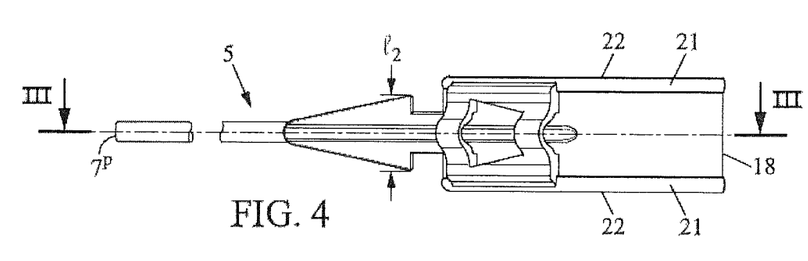
FIG. 4 is a bottom view of FIG. 2.

As can be seen in FIG. 3, the distance between the loops (measured between the proximal end of the proximal loop $11_1$ closest to the proximal end $13^P$ of the band and the distal end of the distal loop $11_2$ closest to the distal end $9^d$ of the band) carried by the rectilinear part of the distal part of the hollow flexible band is approximately 38 mm. This represents approximately 21% of the total length of the inner wall of the hollow band measured between the proximal end $13^P$ and the distal end $9^d$.

The hollow flexible band 2 also has two parallel longitudinal radiopaque bands 21 near the longitudinal edges 22 of the outer wall 18. As is shown in FIG. 5, a radiopaque band 24 is also provided on the proximal transverse edge of the hollow flexible band 2.

It will be noted that these longitudinal edges 22, and also the corresponding edges 23 of the inner wall 17 of the hollow flexible band 2, are blunted, even rounded, so as not to present sharp angles liable to injure the patient.

The hollow flexible band 2 has the characteristic of having an outer wall 18 produced from an elastomer material M1, for example biocompatible silicone, with a hardness D1, while the inner wall 17 is produced from an elastomer material M2, for example biocompatible silicone, with a hardness D2 lower than D1. In practice, D1 is equal to 0.5×D2, for example. The outer wall 18, thus reinforced, permits better control of the stomach restriction during the inflation of the hollow flexible band 2 placed in a stable manner around the stomach.

The hollow flexible band 2 is produced by molding in one piece with the two constituent materials M1 and M2: M1 for the outer wall 18, having at least two loops in the distal rectilinear part of the hollow flexible band, and M2 for the inner wall 17, although there can also be a third material M3 corresponding to the parallel radiopaque longitudinal bands 21 and to the radiopaque transverse band 24.

The Flexible Tube 5

The distal end $6^d$ of the flexible tube 5 is connected to the hollow flexible band 2 by way of the inflation opening 4 formed in the outer wall 18.

In addition, the flexible tube 5, in its rectilinear part 16 with distal end $6^d$, is equipped with means for looped closure by slip knot, which means are complementary to those $11_1$, $11_2$ of the rectilinear part 15, with distal end $9^d$, of the hollow flexible band 2. The closure means $10_1$, $10_2$ are dovetailed notches whose bases $10_{1b}$ and $10_{2b}$ are of different widths $1_1$, $1_2$. The width $1_1$ of the notch $10_1$ nearest to the distal end $6^d$ is less than the width $1_2$ of the other notch $10_2$.

According to one variant, these widths $1_1$, $1_2$ can be equal.

Once the flexible tube 5 is engaged through and beyond the loops $11_1$, $11_2$, the bases $10_{1b}$ and $10_{2b}$ of the dovetails $10_1$ and $10_2$ are in non-return abutment against the arches $11_1$, $11_2$, in such a way as to lock the hollow flexible band 2 in a ring shape in the closed position, as is shown in FIG. 8.

To further reduce the force needed for the passage of the flexible tube 5, it is also conceivable for the outer surface of the latter to be covered with a coating having a low coefficient of friction.

The proximal free end $7^P$ of the flexible tube 5 can advantageously be closed off by a stopper of conical shape, which prevents introduction of material into the catheter channel and facilitates the introduction of the catheter into the loops $11_1$, $11_2$ during the closure of the hollow flexible band 2 in order to form the ring. After formation of the ring, the surgeon removes the stopper and connects the flexible tube to the inflation means 8.

The Inflation Means 8:

As is shown in FIG. 8, the inflation means 8 are composed of a chamber 80 with implantable catheter, provided with a septum 81 through which a needle can be placed for puncturing and injecting inflation fluid.

The implant according to the invention can be put in place by laparoscopy. To help the surgeon, optical locating means are provided on the hollow flexible band 2 and/or on the flexible tube 5.

Alternative Embodiment with Radiopaque Insert:

According to this variant, the gastric band 1 in question comprises a radiopaque insert 40 lodged in the hollow flexible band 2, said insert 40 preferably having a continuation 41 of at least one of the walls 17-18-19-90-130 of the hollow flexible band 2, and still more preferably a continuation 41 of the distal end wall 42 of the hollow band 2. According to a particularly preferred form of this variant, the gastric band 1 is obtained from an intermediate molded component 1', which is removed from the mold through an opening 91 provided in place of the distal end wall 42 of the hollow flexible band 2, said distal end wall 42 being fixed to the intermediate molded component 1' after demolding, and the distal end wall 42 preferably forming one of the ends of a radiopaque insert 40 lodged in the hollow flexible band 2.

In this preferred form of the variant, the radiopaque insert 40 is composed of a base 42 having a continuation 41, as is shown in FIGS. 11A-11B-12A-12B.

Figure 11A:
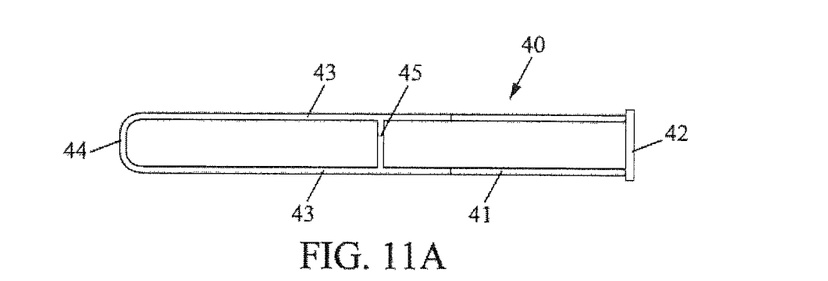
FIG. 11A is a front view of a radiopaque insert intended for the gastric band according to the invention.
Figure 11B:
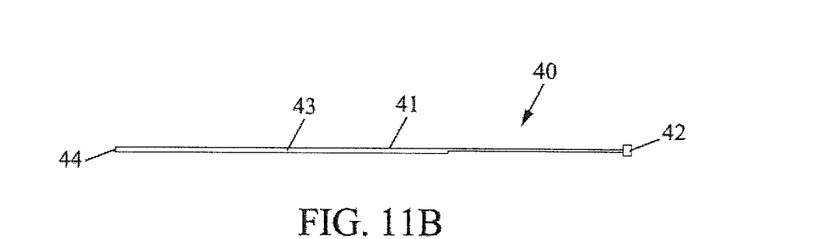
FIG. 11B is a side view of FIG. 11A.
Figure 12A:
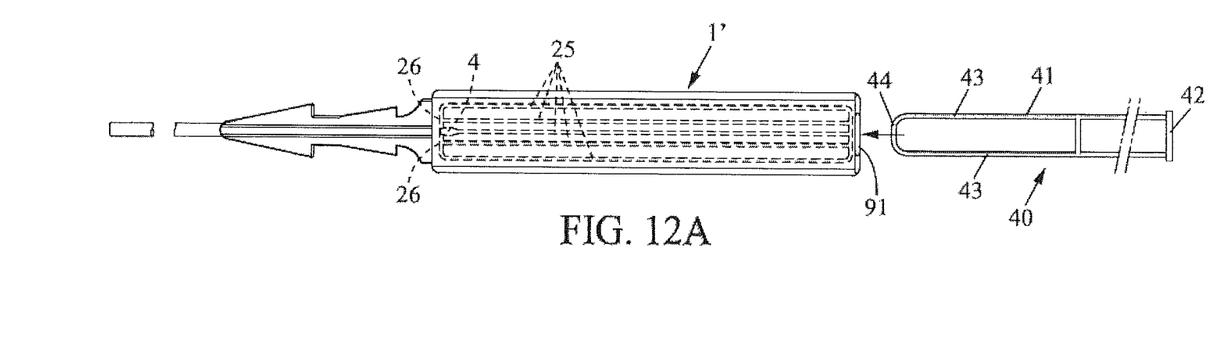
FIG. 12A is a bottom view (inner wall) of the gastric band according to the invention, open at its distal end and prior to completion, and also of the radiopaque insert from FIGS. 11A & 11B prior to its introduction into the gastric band.
Figure 12B:
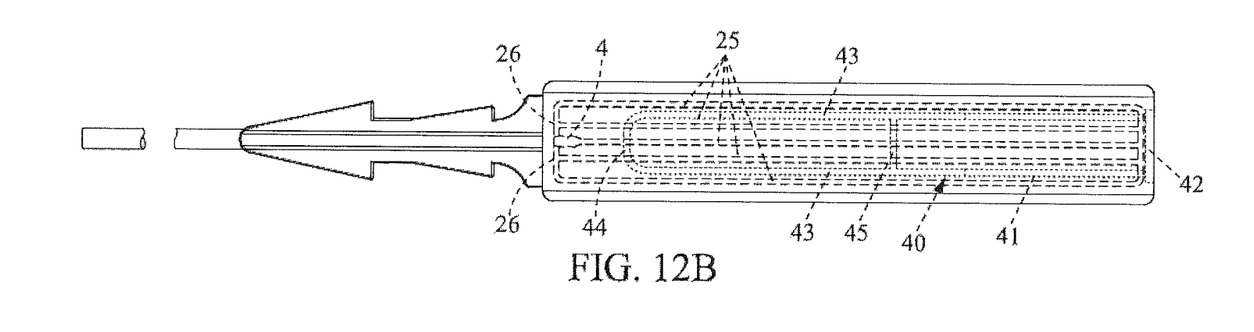
FIG. 12B is a view of FIG. 12A after the introduction of the radiopaque insert from FIGS. 11A & 11B into the gastric band.

The base 42 of the insert 40 can be made from silicone elastomer, for example, while the continuation 41 extending from this base 42 and forming the actual radiopaque part is made from a silicone elastomer charged with a radiopaque material, for example barium sulfate.

As is shown more clearly in FIG. 11A, the continuation 41 is composed, for example, of two parallel rods 43 integrally connected to the base 42 at one of their ends and connected to each other at the free end 44 of the continuation 41. A spacer 45 interconnects the rods 43 of the continuation 41.

This radiopaque insert 40 shown in FIGS. 11A-11B can be introduced inside the hollow flexible band 2 of the gastric band 1 via a demolding opening 91 provided on an intermediate molded component 1', precursor of the finished gastric band 1.

Once introduced into the chamber 30 inside the hollow flexible band 2, the continuation 42 is independent of the hollow band 2, while the base 42 of the insert 40 forms a stopper for closing the opening 91, in order to form the distal end wall 90 of the hollow flexible band 2.

The base 42 (or stopper) can be fixed to the hollow flexible band by any suitable means, for example adhesive bonding, welding, etc.

The continuation 43 advantageously has a length less than that of the chamber 30 of the hollow flexible band 2, so as not to obstruct the inflation opening 4.

Once the hollow chamber 30 is filled with inflation fluid, the continuation 43 of the insert 40 is immersed in the fluid filling this chamber 30 of the hollow flexible band 2.

The invention claimed is:

1. An inflatable and adjustable gastric band to be positioned around a segment of the digestive tract in order to narrow said segment, said gastric band comprising:
a hollow flexible band, which is resilient and comprises an inner wall and an outer wall defining an inflatable leaktight chamber with an inflation opening;
a flexible inflation tube whose distal end is connected to the inflation opening of the band, and whose proximal end is intended to be connected to inflation means;
the tube and the band being provided, in respective distal end areas thereof, with complementary closure means and that are able to mutually engage so as to lock a ring in a closed position, said ring being formed by bringing a distal end and a proximal end of the band together;
the closure means of the tube being at least one notch and the closure means of the band being at least one loop, such that the proximal end of the tube is configured to be engaged through the at least one loop of the band as far as a locked closure position once said at least one notch is brought beyond said at least one loop; wherein the hollow flexible band, when not in use and when the tube and the band are not engaged in each other to form the ring, has a preformed curved part which extends starting from a proximal end area thereof and which is continued via a substantially rectilinear part to the distal end of the band, said substantially rectilinear part has a length between 10 and 40% of the total length of the hollow flexible band for facilitating the engagement of the proximal end of the tube through said at least one loop of the band, and
said at least one loop being arranged on an outer wall of the substantially rectilinear part of the hollow flexible band.

2. The gastric band as claimed in claim 1, wherein an axis of the substantially rectilinear part of the band intersects the distal end area of the tube.

3. The gastric band as claimed in claim 1, wherein the distal end area of the tube has a substantially rectilinear part when not in use and when the tube and the band are not engaged in each other to form the ring.

4. The gastric band as claimed in claim 3, wherein an angle A formed by the substantially rectilinear part of the band (2) and the substantially rectilinear part of the tube is less than or equal to 50°.

5. The gastric band as claimed in claim 3, wherein an angle A formed by the substantially rectilinear part of the band and the substantially rectilinear part of the tube is between 20° and 50°.

6. The gastric band as claimed in claim 3, wherein an angle A formed by the substantially rectilinear part of the band and the substantially rectilinear part of the tube is between 40° and 90°.

7. The gastric band as claimed in claim 3, wherein an angle A formed by the substantially rectilinear part of the band and the substantially rectilinear part of the tube is less than or equal to 60°.

8. The gastric band as claimed in claim 1, wherein the proximal end area of the band is substantially rectilinear.

9. The gastric band as claimed in claim 1, wherein the hollow band is in one piece, and wherein the hollow band is produced from at least two materials M1, M2, which differ from each other at least in terms of their respective hardness D1, D2, with D1 >D2, the material M1 constituting at least part of the outer wall, and the material M2 constituting at least part of the inner wall.

10. The gastric band as claimed in claim 9, wherein the at least two materials M1, M2 are chosen from silicone elastomers.

11. The gastric band as claimed in claim 1, wherein the outer wall of the hollow flexible band comprises longitudinal edges and at least the longitudinal edges of the outer wall are protuberant.

12. The gastric band as claimed in claim 11, wherein the longitudinal edges (22) of the outer wall (18) are at least partially radiopaque.

13. The gastric band as claimed in claim 1, wherein the inflation opening is formed in an outer wall of the proximal end area of the band, and wherein said outer wall has, on its inner face, recesses of which at least some of said recesses are arranged on each side of the inflation opening, said recesses being intended to prevent occlusion of the inflation opening by the inner wall of the hollow band opposite said inflation opening during deflation.

14. The gastric band as claimed in claim 1, comprising a radiopaque insert lodged in the hollow band.

15. The gastric band (1) as claimed in claim 1, wherein the closure means (11) of the band (2) comprises at least two loops arranged on the outer wall (18) of the substantially rectilinear part (15) of the hollow flexible band (2).

16. The gastric band (1) as claimed in claim 1, wherein the length of the substantially rectilinear part (15) of the hollow flexible band (2) is between 17 and 35% of the total length of the hollow flexible band.

17. The gastric band (1) as claimed in claim 1, wherein the length of the substantially rectilinear part (15) of the hollow flexible band (2) is between 21 and 33% of the total length of the hollow flexible band.

18. The gastric band as claimed in claim 3, wherein an angle A formed by the substantially rectilinear part of the band and the substantially rectilinear part of the tube is equal to 45°.

* * * * *